United States Patent [19]

Neuenfeldt et al.

[11] Patent Number: 5,549,675

[45] Date of Patent: Aug. 27, 1996

[54] METHOD FOR IMPLANTING TISSUE IN A HOST

[75] Inventors: Steven Neuenfeldt, Vernon Hills; James Brauker, Lake Villa; Robert Clarke, Libertyville; Victoria Carr-Brendel, Woodstock, all of Ill.

[73] Assignee: Baxter International, Inc., Deerfield, Ill.

[21] Appl. No.: 180,018

[22] Filed: Jan. 11, 1994

[51] Int. Cl.$^6$ .................................................... A61F 2/02
[52] U.S. Cl. ............................... 623/11; 623/66; 424/93.7
[58] Field of Search .................................. 623/11, 12, 66, 623/16; 435/240.2; 424/93 R, 93 U, 93.1, 93.7; 604/890.1–892.1

[56] References Cited

U.S. PATENT DOCUMENTS 5,314,471  5/1994  Brauker et al. ........................... 623/11

OTHER PUBLICATIONS

Webster's New World Dictionary 3rd College edition, ©1988 p. 441.

Primary Examiner—Mary Beth Jones
Assistant Examiner—Robert Clarke
Attorney, Agent, or Firm—Hill, Steadman & Simpson

[57] ABSTRACT

A method for implanting cells into a host tissue is provided. The method comprises the steps of: creating an implant assembly for holding cells including wall means for forming a porous boundary between the host tissue and the implanted cells in the device, the pore size of the boundary being sufficient to isolate the implanted cells from the immune response; implanting the assembly without the cells into a host tissue; and accessing an interior of the assembly to add the cells thereto.

2 Claims, 3 Drawing Sheets

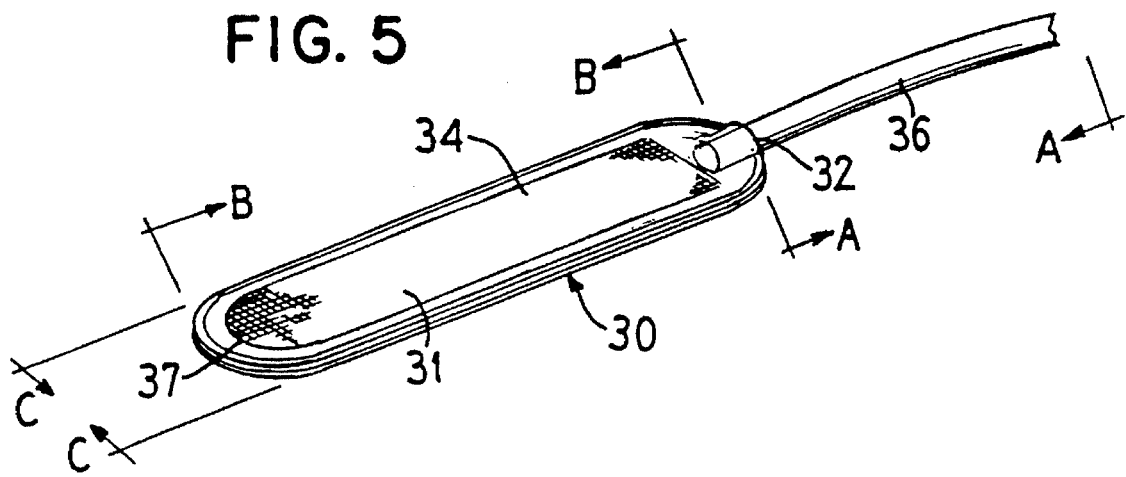
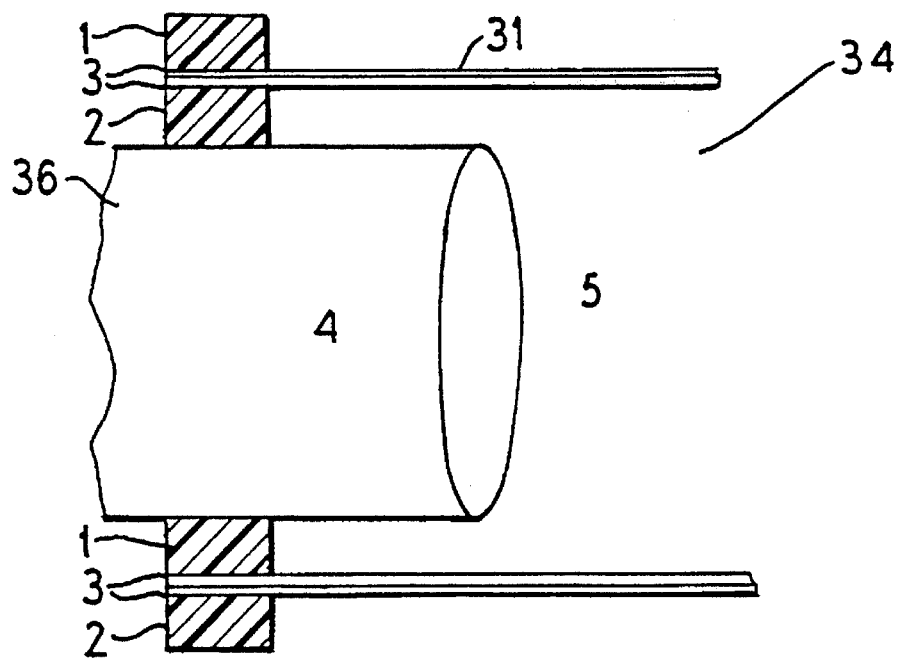

and an exterior surface defining an interface with the host

METHOD FOR IMPLANTING TISSUE IN A HOST

BACKGROUND OF THE INVENTION

The present invention relates generally to the implantation of devices within a host. More specifically, the present invention relates to the implantation of devices into host tissue that can provide therapeutic materials to the host.

Recent attention has focussed on attempting to surgically implant living cells in a host to treat various diseases, as well as molecular deficiencies. Theoretically, the implanted cells will generate biological products that the host, because of disease, injury, or insult cannot produce for itself. In this regard, for example, the implant assembly can contain pancreatic cells that generate insulin that a diabetic host lacks. Additionally, implanted cells can deliver drugs for therapeutic benefit.

One of the difficulties in implant techniques is providing an implant assembly and methodology that keeps the implanted cells alive long enough to provide the intended therapeutic benefit. In some early attempts to implant pancreatic cells, the cells usually died or became dysfunctional within a few days or weeks after implantation.

For a period of time after implantation, the region of the host tissue next to the implant assembly can be characterized as ischemic. Ischemic means that there is not a sufficient flow of blood in the tissue region closely surrounding the implant assembly. This ischemic condition usually exists during the first two weeks of implantation. In many devices that are implanted, most of the implanted cells, contained within the device, fail to live through this period.

During the ischemic period, a foreign body capsule forms around the implanted cells. The capsule consists of flattened macrophages, foreign body giant cells, and fibroblasts. Originally, conventional hypotheses blamed the foreign body capsule for causing implanted cells to die or become dysfunctional during the ischemic period. However, as noted in U.S. Pat. Nos.: U.S. Pat. 5,314,471 U.S. Pat. 5,344,454 and U.S. patent application Ser. Nos.: 07/606,791 now abandoned; 08/356,787 now pending; and 08/210,068 now pending assigned to the assignee of this patent application, it was discovered that this widely held hypothesis was wrong.

Rather, it was discovered that the cells do not die because of the intervention of the foreign body capsule, but instead, the cells died because conventional implant assemblies and methodologies themselves lack the innate capacity to support the implanted cells ongoing life processes during the critical ischemic period, i.e., the period when the host vascular structures are not nearby. During this time period, the implanted cells perish before the host can grow new vascular structures close enough to the implant assembly to sustain the cells.

In view of this discovery, implant assemblies were created that are so constructed and arranged that they support the growth of vascular structures by the host close to the assembly. Moreover, the assemblies provide high permeability for low molecular weight solutes thereby providing a high metabolic transit value. Using such assemblies, the implanted cells can be isolated within the chamber from the immune response of the host tissue. However, the host grows new vascular structures close to the boundary between the host and the assembly. The vascular structures thereby provide sufficient nutrients to the implanted cells, as well as allow the therapeutic agents generated by the cells to enter the host and be useful therein.

In this regard, the implant assemblies are constructed so that cells are sealed within a cell chamber of the assembly. The implant assembly is then implanted within the host tissue. The assembly is so constructed and arranged that a sufficient metabolic transit value is provided to support the metabolic processes of the implanted cells even in the absence of close vascular structures. This allows the cells to survive during the ischemic period. Within a couple of weeks, formation of new vascular structures around the implant assembly will mark the end of the ischemic period. The structure of the assembly allows nutrients from the host tissue to be received by the cells and allows therapeutic agents from the cells to enter the host tissue.

SUMMARY OF THE INVENTION

The present invention provides a new methodology for implanting cells within a host. Pursuant to the present invention, an implant assembly, without the cells to be implanted, is implanted within a host. Preferably, the assembly is allowed to prevascularize. After vascularization of the implant assembly, the cells to be implanted are then added to the assembly.

As used herein, to be "prevascularized" or "vascularized" means that vascular structures from the host tissue have grown near or immediately adjacent the implant assembly. This allows nutrients from the host to enter the implant assembly and therapeutic agents generated within the implant assembly can enter the vascular system of the host tissue.

It should be noted, however, that the cells can be added before the assembly has prevascularized.

In an embodiment, a method for implanting cells into a host tissue is provided comprising the steps of: implanting an implant assembly for holding therapeutic cells including wall means for forming a porous boundary between the host tissue and the therapeutic cells in the device, the pore size of the boundary being sufficient to isolate the therapeutic cells from the immune response; the assembly is implanted without the therapeutic cells into a host tissue; and accessing an interior of the assembly to add the select cells thereto.

In a preferred embodiment, the assembly is allowed to prevascularize before the select cells are added thereto.

In an embodiment, the interior is accessed by removing an end portion of the assembly.

In an embodiment, the interior is accessed by use of a port means.

In an embodiment, the interior is accessed by use of a syringe or cannula.

In an embodiment, the select cells are added to the assembly at least 21 days after implantation.

In an embodiment, the select cells are added after one day (24 hours).

In an embodiment, the assembly includes a source of angiogenic material when it is implanted.

In an embodiment, the interior of the assembly is empty when it is implanted.

In an embodiment, a method for implanting select cells in a host tissue is provided comprising the steps of: providing an implant assembly including wall means having an interior surface defining a chamber for holding cells for implantation tissue, the exterior surface having a confirmation that results in growth of vascular structures by the host tissue close to the interface; implanting the implant assembly in host tissue without the select cells; allowing vascular structures of the host to grow close to the interface of the assembly; and accessing an interior of the assembly to add select cells thereto.

In an embodiment, an implant assembly and tissue matrix is provided.

It is an advantage of the present invention to provide a method for implanting cells within a host.

Another advantage of the present invention is to provide a method for allowing an implant assembly to be prevascularized before the cells are added thereto.

Furthermore, an advantage of the present invention is to provide an implant assembly that is integrated into the host prior to foreign cells being added thereto.

Moreover, an advantage of the present invention is to provide a method for implanting cells within a host tissue that increases the likelihood that the cells survive within the host.

Additional features and advantages of the present invention are described in, and will be apparent from, the detailed description of the presently preferred embodiments and the drawings.

BRIEF DESCRIPTION OF THE DRAWINGS

FIG. 5 illustrates another embodiment of an assembly that can be used to implant cells pursuant to the techniques of the present invention.

FIG. 6 illustrates schematically portions of the ported device of FIG. 5.

DETAILED DESCRIPTION OF THE PRESENTLY PREFERRED EMBODIMENTS

Figure 1:
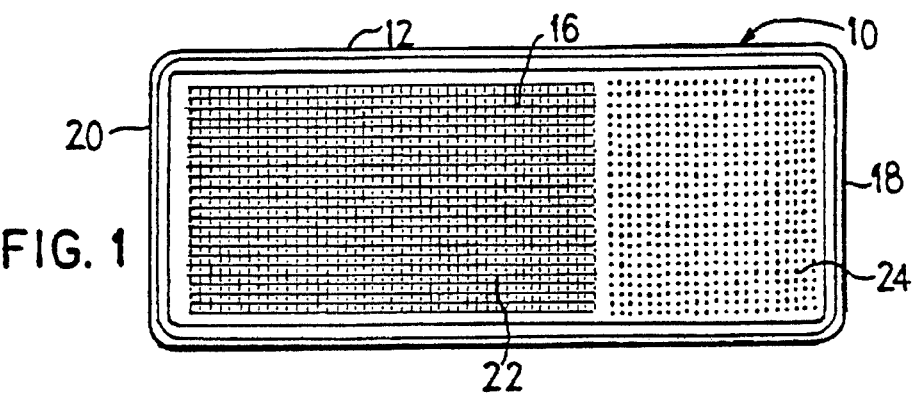
FIG. 1 illustrates an embodiment of an assembly that can be used to implant cells pursuant to the present invention.

The present invention provides a methodology for implanting tissue within a host. The method and apparatus of the present invention is capable of supporting living tissue or cells implanted into human tissue or an animal host.

Pursuant to the present invention, an implant assembly is provided having an interior for receiving cells or tissue. Preferably, the implant assembly is implanted in a host. The implant assembly is allowed to prevascularize, i.e., vascular structures are allowed to grow adjacent to the implant assembly. The interior of the assembly is then accessed allowing a surgeon to place the cells to be implanted in the host therein. The assembly is then closed allowing the cells to provide therapeutic agents to the host. Due to prevascularization, nutrients, as well as removal of waste products, is accomplished by the vascular system of the host. Prevascularization will aid in graft tissue survival.

However, if desired, cells can be added to the assembly before the assembly is entirely vascularized.

Referring now to FIGS. 1–4 which are en face views of the interior of a rectangular assembly, an assembly 10 that can be used pursuant to the present invention is illustrated. The assembly 10 provides a device that allows a method for implanting living cells within soft tissue of a host. For example, the implant assembly 10 can receive clusters of pancreatic cells which can generate insulin for release into and use by a diabetic host.

The assembly 10 forms a porous, life sustaining boundary between the implant cells and the host. The porous boundary isolates the implant cells from attack and destruction by certain biological mechanisms of the host. At the same time, the porous boundary associates with the host biological system closely enough to transfer nutrients and waste in support of the biological processes of the implanted cells. The porous boundary also transfers the therapeutic products generated by the implanted cells to the host.

As illustrated, the implant assembly 10 will include wall members 12 that define the porous boundary. To this end, the walls are defined by porous elements. The porous elements provide certain physical characteristics selected to protect and sustain the viability of the cells within the host. This allows a boundary between the biological system of the host tissue living outside the chamber 16 and the biological system implant cells that will be within the chamber to be created.

FIG. 5 illustrates another embodiment of the assembly 30 of the present invention. The assembly 30 also includes wall members 31 that define a porous boundary. This assembly, as well as the assembly 10 of FIG. 1, will be discussed in more detail hereinafter.

By way of background, for a period of time after implantation, the region of the host tissue immediately surrounding the implant assembly is ischemic. The region is ischemic because the host tissue treats the assembly as a foreign body. The host forms a wound area around the assembly. The wound area has spaces that become filled with wound exudate. The wound exudate keeps the area ischemic. Soon after implantation, host inflammatory cells enter and occupy the area of the exudate. Inflammatory cells include macrophages, foreign body giant cells, and fibroblasts.

The inflammatory cells try to remove the foreign implant assembly. Macrophages from the host try to ingest the foreign implant assembly. In some cases, the macrophages coalesce to form multinucleated giant cells. Fibroblast layers form to create a fibrous sac of cells and collagen around the foreign implant assembly, commonly called the foreign body capsule.

It has been found, as noted in the other patent applications of the assignee that are identified in the background of the invention, that it is not the foreign body capsule that most threatens the viability of the implanted cells during the ischemic period. Rather, the existence of the cells is most threatened during the ischemic period when the boundary itself fails to allow enough extracellular nutrients, such as glucose and other metabolic support compounds present at the boundary to pass through the cells. Without metabolic support, the implant cells become dysfunctional or perish.

In this regard, the wound exudate forms a fluid barrier between the vascular system of the host and the boundary. This barrier hinders the extracellular passage of nutrients from the host vascular system to the boundary. The concentration of nutrients decreases as they transit the exudate barrier to reach the boundary.

As time passes, host endothelial cells will enter the region. These cells begin the crucial process of forming the new vascular structures. However, the host endothelial cells further reduce the availability of nutrients for cells that may be implanted within the device. The ischemic period will end if enough neovascular structures from the host grow within the exudate region close to the boundary of the assembly. When this is accomplished, vascularization of the assembly has occurred. The time period is approximately seven days to twenty-one days depending on the host tissue and implant assembly. However, adding the cells at any time after initial implantation of the device increases the likelihood that the cells will survive and remain viable because vascularization of the assembly has begun.

The assemblies of the present invention provide structures that are characterized in terms of their pore size, ultimate physical strength, and metabolic transit value. U.S. patent application Ser. No. 08/210,068, the disclosure of which is incorporated herein by reference, discloses the characteristics that should be provided by the walls of the assembly. In this regard, the walls will have a pore size sufficient to isolate the implant tissue cells from the immune response of the host. The threshold requirement is that the pore size is selected so that the boundary is impermeable to vascular structures that form close to the boundary. Penetration of the pores by the vascular structure breaches the integrity of the boundary, this can expose the implant cells to the complete immune response of the host. Generally speaking, pore sizes less than about 2 μm will block the ingress of vascular structures.

As noted in U.S. patent application Ser. No. 08/210,068, the ultimate pore size selected also depends upon the species of the host and the biological relationship between the host and the donor of the implant tissue cells. When the cells to be implanted are from another animal species (xenograft), the pore size must be sufficient to prevent the passage of both inflammatory cells and molecular immunogenic factors from the host into the implant tissue chamber. Pore sizes sufficient to block passage of both inflammatory cells and molecular immunogenic factors in the humans lie in the range of 0.015 μm.

When the cells to be implanted are from the same animal species but have a different genetic makeup (allograft), the pore size usually must be sufficient to prevent the passage of only inflammatory cells from the host into the implanted cell chamber. In such cases, the molecular immunogenic factors do not appear to adversely effect the viability of the implanted cells. Pore sizes sufficient to prevent passage of inflammatory cells in humans lie in the range of below about 0.8 μm.

When the cells to be implanted are autologous implants or genetically engineered cells, the pore size must be sufficient to only prevent the cells from entering the host. However, again, the pore size must be selected to prevent ingress of the vascular structures.

The boundary, or walls, of the assembly must have an ultimate strength sufficient to withstand, without rupture, the growth of new vascular structures. Additionally, the boundary must be sufficient to withstand the growth of new cells within the chamber and other physiological stresses close to the host tissue. Keeping the boundary secure assures isolation of the implanted cells from both the immunogenic factors and inflammatory cells of the host.

The boundary also needs to have a metabolic transit value that sustains a flux of nutrients into the chamber and waste products from the chamber. This metabolic transit value should preferably be sufficient to sustain the viability of the implanted cells during the ischemic period. Thus, the cells can be added to the interior before complete vascularization of the assembly, if desired. To calculate the metabolic transit value, the permeability value and porosity value of the boundary are determined.

The permeability value is the measure of the amount of solute that travels through the boundary per unit time and unit surface area. Porosity represents the space in the boundary that does not contain material or is empty and composed of pores. As noted in U.S. Ser. No. 08/210,068, above a threshold minimum porosity value, the permeability value is the principal influence upon the overall metabolic transit value. Below the threshold minimum porosity value, the metabolic transit value must also take into account the porosity value of the physical structure of the porous boundary. As noted in that patent application, to simplify the selection of the boundary, the inventors recommend the use of boundaries having a porosity value greater than the observed minimum threshold value. Then, the metabolic transit value and permeability value can be treated as same.

Referring now to FIGS. 1–4, in the embodiment of the assembly 10 of the present invention illustrated therein, the walls 12 define a chamber 16 that can receive cells. The assembly 10 further includes a first end 18 and a second end 20. In use, the assembly 10 is implanted in a host. The assembly 10 is implanted in the host without the desired cells that one wants to implant. As noted hereinafter, however, if desired, cells that stimulate vascularization can be added to the interior prior to implantation.

After implantation, the cells to be implanted can be added to the assembly 10. In a preferred embodiment, the assembly is allowed to prevascularize before the cells are added.

To this end, after a sufficient time period, e.g., after prevascularization, a surgeon accesses the first end 18 of the assembly 10 by making the necessary incision in the patient. The assembly 10 is then opened by removing the first end 18 of the assembly 10. The end of the assembly can be removed by the surgeon cutting same or by the use of frangibles or other means.

In an embodiment, not illustrated, the first end can include a duck bill valve. This will allow the surgeon to access the interior of the assembly without cutting off an end of the assembly.

In an embodiment, to maintain the integrity of the chamber 16, the assembly 10 will include at least one insert. In the illustrated embodiment, two inserts 22 and 24 are provided: a tissue cavity insert 22; and a polymer spacer 24. The tissue cavity insert 22 maintains the integrity of the cavity during prevascularization and the polymer spacer 22 is used to maintain the location of the tissue in the cavity.

Figure 2:
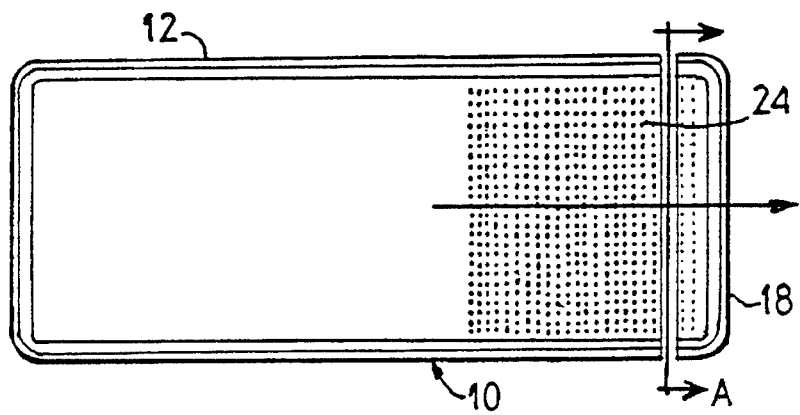
FIG. 2 illustrates the assembly of FIG. 1 opened to provide access to an interior of the assembly.
Figure 3:
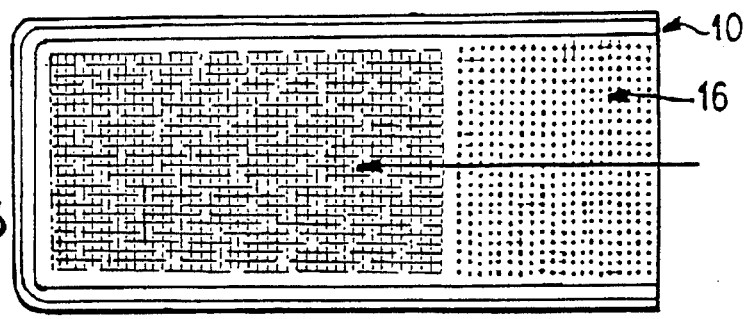
FIG. 3 illustrates the assembly of FIG. 1 with tissue placed in the interior thereof.
Figure 4:
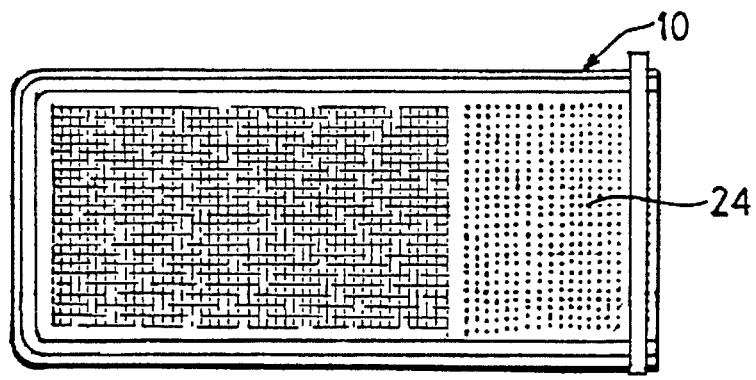
FIG. 4 illustrates the assembly of FIG. 1 after it has been sealed.

To add tissue to the assembly 10, after it has been implanted, the surgeon after removing the first end 18, as illustrated in FIG. 2, will remove the inserts 22 and 24. The surgeon will then place the tissue to be implanted in the assembly 10, as illustrated in FIG. 3. In the preferred embodiment illustrated, the polymer insert 24 will then be placed in the assembly. As illustrated in FIG. 4, the assembly 10 will then be closed using a heat seal, plug, or mechanical means. The wound can then be closed. The assembly 10, which was implanted without the cells to be implanted, now includes tissue. Because vascularization of the assembly 10 has begun, or indeed may be complete, the likelihood of maintaining viability of the implanted cells within the assembly is increased.

FIG. 5 illustrates another embodiment of an assembly 30 that can be used in the present invention. This assembly is discussed in detail in U.S. patent application Ser. No. 07/861,952 entitled: "PORTED TISSUE IMPLANT SYSTEMS AND METHODS OF USING SAME" that is being filed on the same day as this application naming Steven Neuenfeldt, James Brauker, and Robert Clarke as inventors now U.S. patent application Ser. No. 08/356,787. The disclosure of that application is incorporated herein by reference.

In the embodiment of FIG. 5, the assembly 30 includes a port member 32 that provides means for accessing the interior or cell chamber 34 of the assembly 30. In the embodiment illustrated, the port member 32 is an elongated flexible tube 36. The elongated flexible tube is in fluid communication with the cell chamber 34 that is defined by the walls 31 of the assembly.

It should be noted, however, that the port member 32 does not have to be defined by an elongated flexible tube. Other structures can be used to provide access to the cell chamber of the assembly 30. For example, a resealable injection site can be provided on the assembly for providing access to the cell chamber.

By providing a port on the assembly, the port can be used to place cells within the assembly 30 after it has been implanted. In this regard, a cannula or other device can be used to place the cells within the cell chamber 34 defined by the assembly 30.

To this end, in an embodiment, the assembly 30 is implanted with the flexible tube 36 being located near the outer epidermal layers of the patient. To implant cells in the assembly 30, a surgeon merely creates an incision in the skin exposing the end portion of the flexible tube 36. This allows the surgeon to thereby access the interior of the assembly 30 utilizing a cannula or other method for depositing new cells within the cell chamber 34 of the assembly 30 through the flexible tube 36.

In filling the interior of the assembly 30, in an embodiment, a cannula is utilized having a cannula that will be received within the full length of the port 32 and to an end 37 of the cell chamber 34 of the assembly. Using a syringe, as tissue is laid within the chamber 34 of the assembly 30, the cannula is slowly removed from the chamber. This methodology will insure that too great a pressure is not used that will damage the membrane as the tissue is laid. It is believed that the pressure used should be lower than syringe pressures. By using reduced pressure, additionally, this will insure that tissue is not damaged due to frictional forces that can shear the tissue if high pressures are utilized.

After the cells have been placed within the assembly 30, the tube 36 can then be sealed using a heat seal, mechanical means, a silicon plug, or another method. The tube 36 is then placed within the patient and the incision is closed.

Of course, other assemblies that allow cells to be added to an implanted assembly can be used. The principal requirement of such assemblies being that they allow a means for accessing an interior thereof to allow cells to be added to the implanted device.

If desired, an angiogenic material for stimulating neovascularization close to the boundary can be provided. The specific identity of the angiogenic material is not known. Still, the inventors have determined that the presence of certain cells stimulate neovascularization, while others do not.

For example, the presence of: lung tissues; pancreatic islets; adult pancreatic ducts; and cultured cell lines of fibroblasts, mammary gland, and smooth muscle cells induces or stimulates neovascularization, when compared to the vascularization on control grafts where these cell types were not present.

The inventors believe that certain cells induce or stimulate neovascularization by secreting angiogenic factors. Because the stimulus crosses membranes that are impermeable to cells, it must be a molecular signal that the living cell generates.

Accordingly, in an embodiment, although the assembly does not include therapeutic cells at the time of implantation, the assembly does include a separate angiogenic source cell or material.

Alternatively, the practitioner may coat the exterior of the boundary itself with an angiogenic material.

By way of example and not limitation, the following example is provided.

EXAMPLE

This study demonstrates that isogeneic fetal lung tissue survive better in a prevascularized ported device than in the same device without prevascularization.

Materials and Methods

Isolate Fetal Lung Tissue

Day 15 ½ time-pregnant female Lewis rats (ICR) were obtained from Harlan Sprague Dawley (HSD) and were $CO_2$-asphyxiated and cervically dislocated. The ventral abdominal area was swabbed/saturated with 70% ETOH. Using sterile forceps and scissors, the fur was cut away from the abdomen. A second set of forceps/scissors was used to cut through the abdominal muscles into the peritoneal cavity. Both uteral horns were removed and placed immediately into sterile ice-cold HBSS (supplemented with 1% penicillin G [10,000 U/ml]/ streptomycin [10,000 μg/ml]). The embryonic sac was removed from the uterus and the fetus was removed. Fetuses were placed in ice-cold sterile surgical media (DMEM supplemented with 20% FBS, 1% penicillin G [10,000 U/ml]/streptomycin [10,000 μg/ml] and 1% L-glutamine [100 mm]).

Using sterile jeweler's forceps, fetal lungs were dissected, removed, and placed in ice-cold surgical medium.

Tissue Preparation

Lung tissue was collected and placed in a sterile microcentrifuge tube. The excess media was removed, such that the meniscus of the medium was just above the tissue. The lungs were then minced into approximately 1 $mm^3$ pieces. The tissue was then washed with 3 volumes of surgical media. The tissue was then placed into two sterile microcentrifuge tubes. One tube was diluted with an equal volume of surgical media (low density) and excess surgical medium was removed from the other tube such that the meniscus was just above the level of the tissue (high density). The tubes were placed on ice until surgery.

Device Preparation

Ported devices were constructed using materials listed in Table 1. The ported devices were substantially similar to that illustrated in FIG. 5. The overall dimensions for the ported device 30 were as follows: length a=2.5 cm; length b=2.77 cm; and width c=0.58 cm. FIG. 6 details a portion of an assembly 30 schematic identifying in conjunction with Table 1 below the materials used to construct the ported device of this example.

TABLE 1

Materials used in the assembly of the ported devices

| Item | Quantity | Description |
|------|----------|-------------|
| 1 | 2 each | 0.0052" polyester mesh |
| 2 | 2 each | 0.00375" polyester mesh |
| 3 | 2 each | 5 μm Goretex ™ to Biopore ™ membrane laminates |
| 4 | 1 each | Intramedic polyethylene tubing, 0.060" O.D. × 0.034" I.D. × 2.5 cm long |

Membrane Sterilization

Devices were immersed in 95%ETOH until membranes appeared transparent. The devices were then placed in 70% ETOH for overnight sterilization. Devices were washed three times in 0.9% NaCl (saline), with a 20 minute soak included in the second wash. Devices were stored in saline until surgery or loading.

Device Loading In Vitro $23_G$ blunted needles (Popper and Sons, Inc.) were sterilized in 70% ETOH and washed. Additionally, saline was pushed through the needle to wash the inner lumen. Lewis lung tissue was loaded into 1 ml syringes joined with the $23_G$ blunted needle. The ported device was removed from the saline and 10 μl of Lewis lung (low tissue density or high tissue density) was injected into each device.

The port (polyethylene [PE] 100 tubing, Intramedic) was then sealed with a heated hemostat. The excess PE was removed. The devices were placed in sterile surgical medium at 37° C., 5% $CO_2$ until surgery.

Device implantation

Ported devices, either filled with tissue or empty, were implanted into the epididymal fat-pad of Lewis rats. The animals were anesthetized with a cocktail of xylazine (Rompun®, Haver Labs, 20 mg/ml)(0.25 mls/g) and ketimine (Ketasset®, Aveco Labs, 100 mg/ml)(0.65 mls/kg). The ventral abdominal area was shaved and swabbed with Providone Iodine Prep Solution. A 1–2 cm incision was made just cranial to the scrotum at the midline with a sterile scalpel. The abdominal muscle layer was cut to the same size as the outer incision. The fat-pad was removed and placed on saline-wetted sterile gauze.

The device was placed on the fat such that the port faced cranially. The device was wrapped in fat and secured with small amounts of methylmethacrylate wetting glue (VET-Bond™, 3M). The fat-pad was then returned to the peritoneum. The abdominal wall was sutured together using 4.0 gut and a running stitch. The surface incision was sealed with wound clips. The entire abdominal area was re-swabbed with iodine solution.

Devices were explanted at 3 weeks and placed in 2% glutaraldehyde in Sorensen's buffer. Histological sections were obtained. The sections were stained with hematoxylin and eosin (H & E) and examined by light microscopy.

Device Loading In Vivo

Animals underwent surgery as described in "Device implantation" to expose the implanted device. The device within the fat-pad was placed onto saline-wetted gauze. On occasion, the entire fat-pad, containing the device, could not be dislodged from within the peritoneum, so only the port was exposed. The port was gently scraped of any adhered host tissue and the end clipped off. A $23_G$ blunted stainless steel surgical needle (Popper and Sons, Inc.) on a 1 ml syringe filled with the appropriate tissue, was inserted by gently rotating the needle into the device. 10 μl of the tissue was injected as the needle was withdrawn, gently spinning and removing the needle.

The port was sealed with a heated, sterile hemostat. Excess PE was removed, and the fat-pad was returned to the peritoneum. The animal's surgical site was closed as described in "Device implantation". Devices were explanted, fixed, and stained as described in "Device implantation."

Scoring Histological Sections

H&E stained histological sections were analyzed for tissue survival. The scoring system for internal tissue survival of epithelial cells is described in Table 2 below:

TABLE 2

| Score | Histological Appearance of Implanted Tissue |
|-------|---------------------------------------------|
| 1 | No Living Tissue |
| 2 | Scattered Living cells, mostly dead cells |
| 3 | Less Than 50% of cells alive |
| 4 | More Than 50% of cells alive |
| 5 | Living epithelial cells predominate |
| 6 | Differentiated tissues |

RESULTS

Survival of Isogeneic Tissues Was Improved by Prevascularization

Figure 7A:
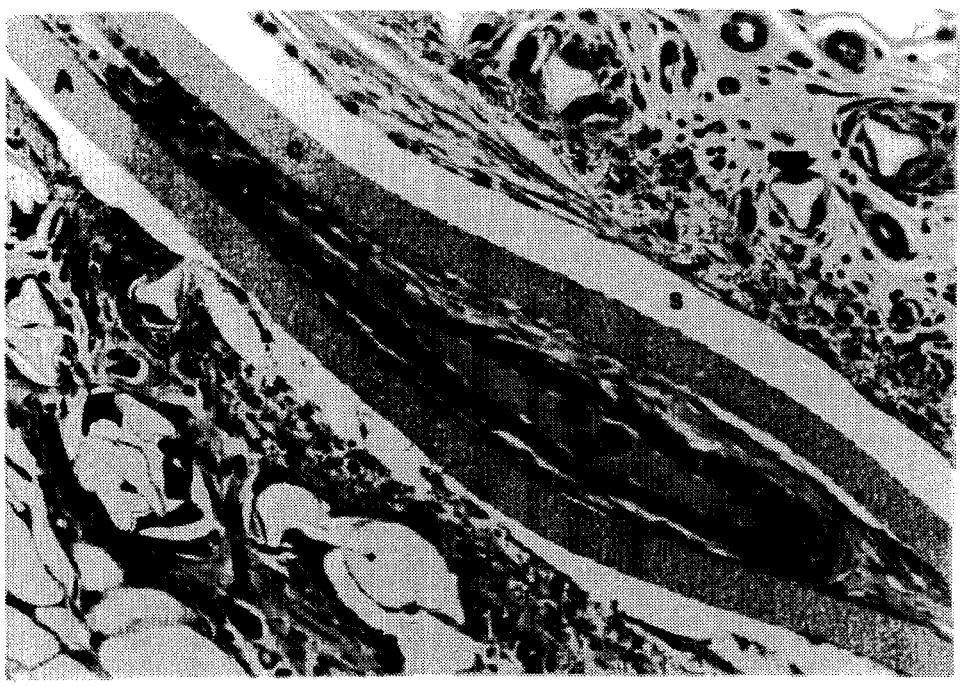
FIGS. 7a is a stained histological section of isogenic fetal lung tissue implanted pursuant to the example set forth hereinafter with a non-prevascularized ported device (A).
Figure 7B:
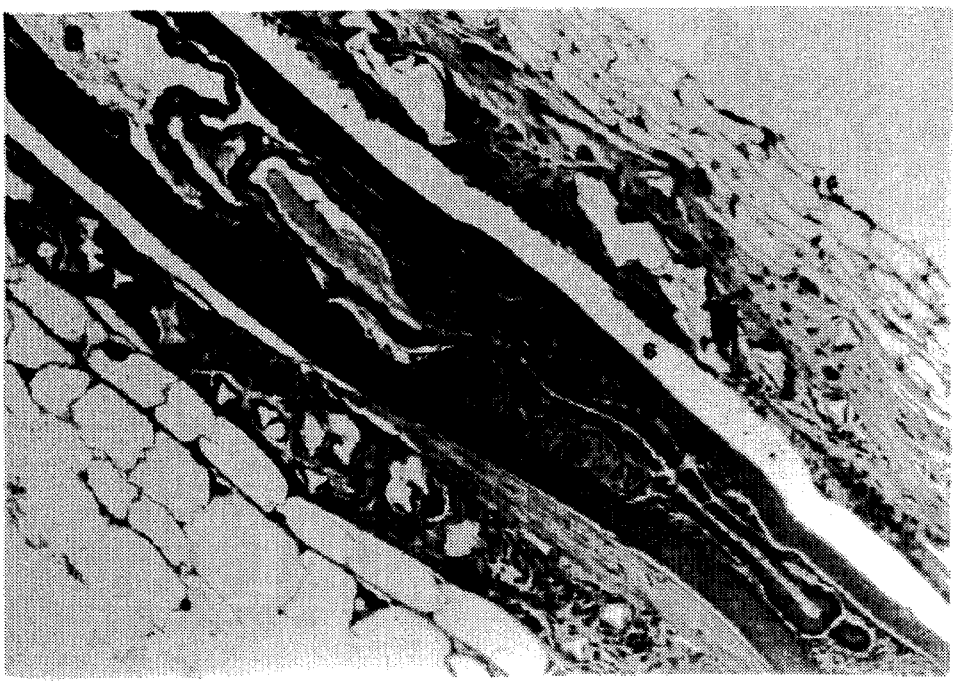
FIG. 7b is a stained histological section of isogenic fetal lung tissue implanted pursuant to the example set forth hereinafter with a prevascularized port device (B).

Lung tissue implanted for 3 weeks without prevascularization had fair survival scores (Table 3, FIG. 7a) (mean score=3.9). However, when the implant was prevascularized, a substantial improvement in survival of the tissue was observed (Table 3, FIG. 7b) (mean score=5.5). The prevascularized devices scored the same as non-prevascularized chambers that are disclosed in U.S. patent application Ser. No. 08/210,068, hereinafter referred to as "Bogg's chambers" (see Table 3).

These data demonstrate enhanced tissue survival in a prevascularized device as compared to a non-prevascularized device.

TABLE 3

Internal tissue survival of isogeneic lung tissue, loaded into prevascularized and non-prevascularized ported devices. Devices were implanted into the fat-pad of male, Lewis rats and explanted at 3 weeks.

| Device | Internal Tissue Survival* | | | | |
|--------|---|---|---|---|---|
| | Raw Score | | | | Mean |
| Non-prevascularized | 4.5 | 4.0 | 3.5 | 4.5 | 3.9 |
| | 3.5 | 3.5 | | | |
| Prevascularized | 5.5 | 4.5 | 4.0 | 6.0 | 5.5 |
| | 6.0 | 6.0 | 6.0 | 6.0 | |
| Bogg's Chamber | 5.0 | 5.0 | 5.0 | 5.0 | |
| | 6.0 | 6.0 | 6.0 | 5.0 | 5.5 |
| | 6.0 | 6.0 | 6.0 | | |

*The load of tissue, either high or low density, did not change the internal tissue survival scores. Therefore, these data are combined and listed as non-prevascularized and prevascularized devices.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for implanting cells into a host tissue comprising the steps of:

implanting an implant assembly for holding cells including wall means for forming a porous boundary between the host tissue and the implanted cells in the device, the pore size of the boundary being sufficient to isolate the implanted cells from the immune response, the assembly being implanted without the cells into a host tissue;

allowing the assembly to be prevascularized; and adding to an interior of the assembly the cells by use of a cannula, by inserting the cannula from a first end of the chamber to a position near a second end of the chamber and adding cells to the chamber as the cannula is removed therefrom.

2. A method for implanting select therapeutic cells in a host tissue comprising the steps of:

implanting an implant assembly including wall means having an interior surface defining a chamber for holding select therapeutic cells for implantation and an exterior surface defining an interface with the host tissue, the exterior surface having a confirmation that results in growth of vascular structures by the host tissue close to the interface, the assembly being implanted in host tissue without the select therapeutic cells; and adding, after implantation, to the assembly the select therapeutic cells using a cannula, by inserting the cannula into the chamber for an entire length of same and adding select therapeutic cells to the chamber as the cannula is removed therefrom.

* * * * *